United States Patent [19]
Gutierrez et al.

[11] Patent Number: 4,664,826
[45] Date of Patent: May 12, 1987

[54] METAL SALT ESTERS OF HYDROCARBYL SUBSTITUTED SUCCINIC ACID OR ANHYDRIDE AND THIO ALKANOLS

[75] Inventors: Antonio Gutierrez, Mercerville; Stanley J. Brois, Westfield; Jack Ryer, East Brunswick; Harold E. Deen, Cranford, all of N.J.

[73] Assignee: Exxon Research & Engineering Co., Florham Park, N.J.

[21] Appl. No.: 763,294

[22] Filed: Aug. 7, 1985

Related U.S. Application Data

[63] Continuation-in-part of Ser. No. 359,801, Mar. 19, 1982, abandoned, which is a continuation-in-part of Ser. No. 194,067, Oct. 5, 1980, abandoned.

[51] Int. Cl.$^4$ ........................................ C10M 129/72
[52] U.S. Cl. .................................. 252/482; 560/195; 560/196; 560/198; 252/49.7; 252/51; 252/56 D; 252/389.61; 252/392; 252/395; 252/396; 252/400.61; 252/403; 252/406; 252/407

[58] Field of Search ................. 252/56 D, 48.2, 39.51, 252/49.7; 560/195, 196, 198

[56] References Cited

U.S. PATENT DOCUMENTS 3,045,042  7/1962  Staker ............................... 252/56 D
3,117,091  1/1964  Staker ............................... 252/56 D Primary Examiner—Jacqueline V. Howard
Attorney, Agent, or Firm—R. A. Maggio

[57] ABSTRACT

The present invention provides certain metal (e.g., Ca or Mg) ester salt derivatives capable of exhibiting friction modification, oxidation inhibition, and corrosion inhibition properties in power transmitting fluids such as automatic transmission fluids. These salts are derived from mono or diesters prepared by the reaction of an alkanol (e.g., thio-bis-ethanol) and a hydrocarbon substituted succinic acid or anhydride, such as octadecenyl succinic anhydride.

54 Claims, No Drawings

METAL SALT ESTERS OF HYDROCARBYL SUBSTITUTED SUCCINIC ACID OR ANHYDRIDE AND THIO ALKANOLS

CROSS-REFERENCE TO RELATED APPLICATIONS

This application is a continuation-in-part of U.S. application Ser. No. 359,801, filed Mar. 19, 1982 which is a continuation-in-part of U.S. application Ser. No. 194,067, filed Oct. 5, 1980, both now abandoned. The disclosures of all the above-identified patent applications are herein incorporated by reference. U.S. Pat. No. 4,344,853, issued Aug. 17, 1982, which is also a continuation-in-part of U.S. application Ser. No. 194,067, discloses and claims zinc and nickel salts of the esters of thio-bis-alkanols and antioxidants.

A composite of U.S. Pat. No. 4,344,853 and U.S. application Ser. No. 194,067 was published on Apr. 9, 1982 as French Publication No. 2,491,492 (see U.K. Pat. No. 2,085,918 for this English text counterpart).

BACKGROUND OF THE INVENTION

The present invention relates to certain multi-functional metal salt derivatives of certain heteroatom, e.g., sulfur, containing esters, compositions containing the same suitable for use as, inter alia, automatic transmission fluids (ATF), and methods for preparing and using such compositions.

At the inception of automatic transmissions, conventional mineral oils were employed, with optional oxidation inhibitors, to lubricate such transmissions. As service experience increased, however, it became evident that such oils were inadequate, and that a special type of lubricant was needed.

Thus, the automotive industry began to establish the requirements of acceptable AT Fluids. In 1973 General Motors introduced the DEXRON® II specifications which an ATF had to meet to be qualified for use in their automatic transmissions. Likewise, in 1960 Ford developed their M2C33-D specification, replaced it in 1967 with their current Type F fluid specifications, and in 1975 issued a M2C138 CJ specification for a friction modified fluid.

Conventional requirements of AT Fluids include the capability of: transmitting power in the torque converter; lubricating gears and bushings; removing heat efficiently; insuring transmission seal performance; operating at temperatures of from about −40° to about 175° C.; exhibiting high oxidation resistance, non-corrosiveness toward transmission components, and anti-foam properties.

Oxidation stability permits the avoidance of the formation of sludge and/or varnish during the normal drain period of the fluid.

High and low temperature operability relate to the ability of the ATF to remain shear stable at elevated temperatures and also exhibit acceptable viscosity or fluidity at low temperatures.

Seal performance relates to the ability of the ATF to avoid causing excessive swelling, shrinking, hardening or cracking of the rubber seals used in the transmission. However, AT Fluids should cause a slight seal swelling to produce a tighter fit, thereby reducing fluid leakage past the seals. The majority of seals used in automatic transmissions are nitrile, silicone, and polyacrylic elastomers.

Lubrication performance relates to the oiliness and lubricity of the fluid. Proper oiliness is necessary to allow smooth engagement of composition clutch plates with steel reaction plates. Too little oiliness results in "squawk" and rough shifting and too much oiliness results in slippage of clutch plates and ultimately in excessive wear. Adequate lubricity is required to insure proper lubrication of transmission parts to prevent scoring and wear.

Foam inhibition is required as a result of the severe foam producing conditions, such as, extensive turbulence and air entrainment in the transmission. Foaming is undesirable in several respects. In order for the fluid to perform with maximum efficiency as a hydraulic fluid, it must remain relatively incompressible. Hence, any air trapped in the fluid can cause changes in pressure which, in turn, may result in excessive clutch slippage and wear. Foam can also cause pump cavitation and wear. It also permits a more intimate contact of air with the fluid, thus promoting oxidation. Foam inhibitors are usually oil insoluble, finely dispersed materials which reduce the surface tension of the fluid, thereby allowing the trapped air to escape more readily through the fluid surface.

Corrosion inhibition is an ATF requirement which is typically associated with the problem of the deterioration of copper and brass parts located in the transmission. Typically, copper and brass react adversely to hydrogen sulfide and/or mercaptan compounds present in the AFT. Such corrosion can cause malfunctioning of the transmission.

The above-discussed characteristics of AT Fluids are basic to all such fluids.

In contrast, one of the most complex and demanding property to incorporate into an ATF is the proper friction characteristic. This property distinguishes AT Fluids from other lubricants, and in fact between types of ATF as well. This characteristic quality has received the most attention by both the transmission manufacturers and fluid producers for many years. This stems from the fact that the friction requirements of an ATF are unique and depend on the transmission and clutch design, as well as on the type of clutch plate material used.

Accordingly, various tests have been designed by auto manufacturers for measuring ATF friction properties which if passed is indicative of the fact that such properties will match the requirements of particular transmission designs and result in smooth shifting under a variety of road conditions.

Very recently, more stringent requirements relating to friction modification of AT Fluids have been set by one or more auto manufacturers as a result of fuel economy goals. The desire to enhance fuel economy has resulted in increased usage of converter clutches, a shift to front wheel drive, and the downsizing of cars and power trains. In addition, the use of asbestos-free clutch plates, and continuously variable transmissions are becoming more widespread. Thus, transmission designs have undergone radical changes, thereby necessitating the formulation of ATF friction modifier additives capable of meeting new and more stringent friction property requirements needed to match such design changes.

As indicated above, no base oil alone can even approach the many special properties required for ATF service. Consequently, it is necessary to employ several chemical additives, each of which is designed to impart or improve a specific property of the fluid. Many of these additives, however, are multifunctional, and in such instances it is not necessary to use a separate additive for each purpose.

Accordingly, there has been a continuing search for new additives possessed of one or more properties which render them suitable for use in ATF compositions. The present invention is a result of this search.

The prior art contains a wide variety of compounds useful for friction modification in lubricating oils and in ATF. Representative disclosures are U.S. Pat. No. 3,933,659 which discloses fatty acid esters and amides as friction modifiers for functional fluids; U.S. Pat. No. 4,176,074 describes molybdenum complexes of polyisobutenyl succinic anhydride-amino alkanols as friction modifiers; U.S. Pat. No. 4,105,571 discloses glycerol esters of dimerized fatty acids as friction modifiers in lubricating oils.

Diesters of monohydric alcohols, including those with sulfur linkages, which have been esterified with $C_3$-$C_{24}$ alkenyl succinic acid are disclosed in U.S. Pat. No. 2,561,232. The diesters disclosed therein are said to be useful as synthetic lubricant fluids. U.S. Pat. Nos. 3,198,737 and 3,278,566 disclose fatty esters having utility as extreme pressure agents. U.S. Pat. No. 2,540,570 discloses glycol esters of rosin or other fatty acids with thioglycols, the compounds being useful as extreme pressure additives.

U.S. Pat. Nos. 3,045,042 and 3,117,091 both disclose partial esters of alkenyl succinic anhydride with a variety of polyhydric alcohols such as 2,2'-thiodiethanol as rust preventive additives in petroleum fractions such as gasoline and other fuels. U.S. Pat. Nos. 3,576,847 and 3,556,997 disclose sulfinyl-containing alkenyl succinates useful as dispersants, corrosion inhibitors and anti-wear agents in lubricating oil and fuel compositions. U.S. Pat. No. 3,381,002 generally discloses esters of $C_{50}$ and higher hydrocarbon succinic acids suitable as additives in oils and fuels as well as being suitable plasticizers, detergents and emulsifiers.

U.S. application Ser. No. 359,801, by the inventors herein, discloses and claims power transmitting fluid compositions containing the free ester of certain of the additives of the present invention.

SUMMARY OF THE INVENTION

The present invention is based on the discovery that certain metal salt derivatives as described herein are capable of imparting one or more properties to power transmitting fluids, such as automatic transmission fluids, which contain the same. These properties include friction modification, oxidation inhibition, and corrosion inhibition. These properties are enhanced relative to formulations containing the corresponding free ester or no ester at all. In addition, the metal salt derivatives, such as those of Ca or Mg, exhibit a reduced tendency to cause emulsions of the fluids containing the same relative to other metal salt esters, such as nickel ester salts.

The enhanced friction modification properties of the metal salts permits one to use reduced amounts thereof relative to corresponding non-metal containing free esters to achieve similar results. This permits one to flexibly tailor the composition, of for example automatic transmission fluids, to meet the specific requirements of the automotive manufacturers.

Accordingly, in one aspect of the present invention there is provided a composition of matter comprising an alkaline earth metal salt of a monoester compound, diester compound, or mixture of said compounds, said ester compound being formed by the reaction of:

(A) an alcohol represented by the structural formula:

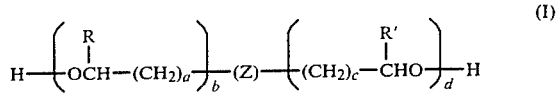

wherein R and R' each independently can represent, hydrogen or $C_1$ to about $C_6$ alkyl; (a), (b), (c), and (d) each independently represent a number which can vary from 1 to about 3; Z represents a linking group selected from —S—; —O—; and >$NR_1$ wherein $R_1$ is selected from hydrogen, $C_1$ to about $C_4$ alkyl, and $C_1$ to about $C_4$ monohydroxy substituted alkyl; and (B) an acid or anhydride represented by the respective structural formulas:

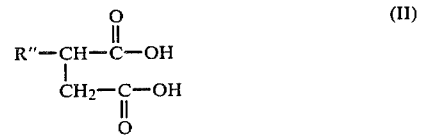

and

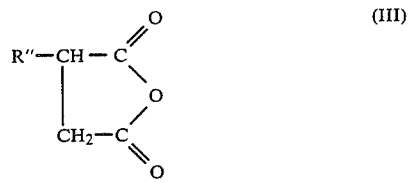

wherein R" is a straight chain aliphatic hydrocarbon group containing from about 12 to about 50 carbons.

In another aspect of the present invention, there is provided a power transmitting fluid containing said metal ester composition.

DESCRIPTION OF PREFERRED EMBODIMENTS

The additives of the present invention are oil soluble metal salts of monoesters, diesters, and/or mixtures thereof, which esters are typically formed by the reaction of (1) an alkanol and (2) a hydrocarbon-substituted succinic acid or anhydride or mixtures thereof.

In one embodiment, the alkanol can be represented by the structural formula:

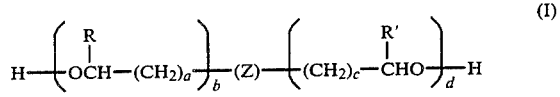

wherein R and R' each independently can represent hydrogen, alkyl (preferably straight chain alkyl), typically $C_1$ to about $C_6$ alkyl, preferably $C_1$ to about $C_3$ alkyl, and most preferably $C_1$ to about $C_2$ alkyl; (a), (b), (c), and (d) each independently represent numbers which can vary from 1 to about 3; and Z is a linking group selected from —S—; —O—; and >$NR_1$ wherein $R_1$ is selected from hydrogen, $C_1$ to about $C_4$ alkyl, preferably $C_1$ to about $C_3$ alkyl, and monohydroxy substituted alkyl, preferably a terminal monohydroxy substituted alkyl, the alkyl being as described immediately above. Preferably, R and R' are the same, the numbers represented by (b) and (d) are the same as are the numbers represented by (a) and (c), thereby resulting in a bis-alkanol.

When Z is —O—, formula I can represent ethylene glycol and derivatives thereof; when Z is >NR$_1$, and R$_1$ is alkyl or hydrogen, formula I can represent a diethanolamine and derivatives thereof; when R$_1$ is a monohydroxy substituted alkyl, such as —(CH$_2$)$_2$—OH, formula I can represent triethanolamine and derivatives thereof.

If b or d are greater than 1, then formula I is meant to express alkoxylated derivatives of the alkanols, such as ethoxylated derivatives. It should be further noted that when diethanolamine or its derivatives as expressed by formula I wherein R$_1$ is hydrogen are reacted with the hydrocarbyl substituted succinic acid or anhydride, the ester product mixture formed thereby can contain an ester-amide moiety, since the NH moiety of diethanolamine is available for reaction with the acid or anhydride moiety. Likewise, when R$_1$ is hydroxy substituted alkyl, the hydroxy substituent of R$_1$ is available for reaction with the acid or anhydride and the reaction product mixture can contain tris-ester moieties.

Notwithstanding the above, while reaction of the R$_1$ substituent with the acid or anhydride is possible, it is not intentionally facilitated. Consequently, the molar amounts of acid or anhydride employed to react with the alkanol are selected as though the R$_1$ substituent is inert, e.g., the acid to alcohol molar ratio will remain within the range of from about 1:1 to about 2:1 as described hereinafter in connection with mono- and di-esters. In such instances, mixtures of ester compounds are typically achieved.

The preferred alkanols are thio-alkanols, wherein in structural formula, I, Z is —S—, and R and R' are independently hydrogen, ethyl or methyl.

The most preferred alkanols are thio-alkanols wherein in structural formula I, (a), (b), (c), are (d) are each 1 or 2, R is hydrogen or methyl, and R' is hydrogen, methyl or ethyl.

Representative alkanols include 2,2'-thiodiethanol; 3,3'-thiodipropanol; thio-bis ethoxyethanol; thio-bis isopropoxy isopropanol; oxy-bis ethanol; oxy-bis ethoxyethanol; 2,2'-diethanol methanamine; 2,2'-diethanol ethanamine; 2,2',2''-triethanolamine; 2,2'-diethanolamine, and mixtures thereof.

The hydrocarbon substituted succinic acid or anhydride which is reacted with the alkanol can be represented by the respective structural formulas:

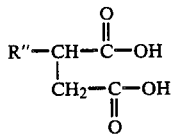

(II)

and

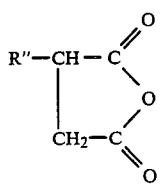

(III)

wherein R'' is an aliphatic hydrocarbon group, typically a C$_{12}$ to about C$_{50}$ aliphatic hydrocarbon group (preferably a straight chain aliphatic hydrocarbon group), preferably a C$_{16}$ to about C$_{30}$ (e.g., C$_{18}$ to about C$_{30}$) aliphatic hydrocarbon group, and, most preferably, a C$_{18}$ to about C$_{22}$ aliphatic hydrocarbon group. The aliphatic hydrocarbon group can be alkyl, preferably straight chain alkyl, alkenyl, preferably straight chain alkenyl, isoalkyl, or isoalkenyl.

Oligomers containing the aforedescribed number of carbon atoms are also suitable as the aliphatic hydrocarbyl group, such as oligomers of C$_2$-C$_5$ monoolefins, such as isobutene.

The aliphatic hydrocarbyl group is preferably unsubstituted hydrocarbon group although it may contain substituents such as chlorine, bromine, sulfur, phosphorous, nitrogen or oxygen which will not affect the utility of the final mono- or di-ester product. A preferred substituent is sulfur as exemplified by 2-octadecylthiosuccinic anhydride.

The hydrocarbyl substituted succinic acid or anhydride compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the mono- and di-ester compounds are C$_{18}$ to C$_{22}$ alkenyl succinic anhydrides, such as octadecenyl succinic anhydride.

As used herein and when the Z group is in fact inert, the term "monoester" or "hemiester" refers to product made from equimolar proportions of said alkanol and a succinic acid or anhydride, that is, one free hydroxyl group remains; while the term "di-ester" refers to those products using a 2:1 molar ratio of acid to alcohol wherein each hydroxyl group of the alkanol is esterified with a hydrocarbyl-substituted or polyolefin-substituted succinic acid or anhydride. In either case, at least one terminal carboxyl group of the succinic acid moiety remains, which is neutralized to form the metal salt derivative of the ester as described herein below.

Formation of the mono- and di-esters employed to make the metal salt derivatives of the present invention proceeds by reacting the appropriate quantities of anhydride (or acid) and alkanol with or without an inert organic solvent diluent and heating and stirring the mixture at about 50° to 150° C. until esterification of the anhydride is complete. Equimolar quantities of each reactant will provide mainly the mono- (or hemi-) ester and reaction of 2 moles of hydrocarbon substituted succinic acid or anhydride per mole of alkanol will provide the di-ester material. Also, products useful in the present invention encompass mixtures of such mono- and di-esters as well as mixtures of mono-esters, diesters, ester-amides and/or tris-esters depending on the identity of Z group when constituting >NR$_1$.

The esterification reaction time is typically controlled to be from about 10 to about 30 minutes.

Insofar as yields are concerned, the reaction of an equimolar ratio of alkanol (wherein Z is inert) and hydrocarbon succinic anhydride will provide a product containing about 80% mono-ester and about 20% di-ester. The di-ester is produced in somewhat higher yields, about 90% of the product being di-ester and about 10% mono-ester when the mole ratio of succinic anhydride to alkanol is 2:1.

The metal salt derivatives of the di-ester compounds of this invention are preferred embodiments exhibiting generally better thermal and oxidative stability and offering better friction modification properties.

In view of the above, a simplified structural formula of the resulting ester product derived from the succinic acid reactant and an alkanol wherein Z is inert, can be represented as follows:

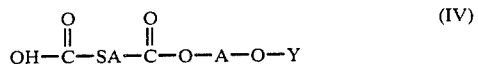
(IV)

wherein SA represents the succinic acid moiety depicted by formula II above exclusive of the terminal carboxyl groups; (A) represents the alkanol moiety depicted by formula I exclusive of the terminal hydroxyl groups; Y represents hydrogen when the product is a hemi-ester, and:

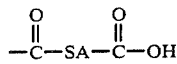

when the product is a di-ester.

The maximum carbon chain length of the R″ substituent is affected by the propensity of increasingly longer chains to come out of solution as the fluid composition containing the same is cooled to lower and lower temperatures. The insolubilization of such substituents is undesirable because it results in agglomeration of the same as well as the formation of nucleation sites for wax crystal formation. Thus, the particular maximum substituent chain length selected will be affected by the ultimate end use for which the additive will be employed in terms of the temperature regimens to which it will be exposed.

Once a suitable ester additive has been prepared, it is converted to the metal salt thereof, said metals being selected from Group IIA of the Periodic Chart, namely, the alkaline earth metals including Mg, Ca, Sr, Ba and mixtures thereof. The preferred metals are calcium and magnesium.

The metal ester salts of the present invention can be prepared by reacting the ester with a metal carboxylate, typically a $C_1$ to about $C_6$ carbon containing metal carboxylate, or a metal hydroxide. Suitable carboxylates include the acetate, propionate, and mixtures thereof. The particular metal containing reactant is typically selected to be at least partially soluble in the reaction mixture solvent containing the coreactant ester.

Suitable solvents are protic and include $C_1$ to $C_5$ alkanols, such as methanol, water, or tetrahydrofuran. The preferred solvent is methanol.

The metal carboxylate or hydroxide is then admixed with the ester in the presence of a suitable solvent in amounts sufficient to meet the stoichiometric requirements of the reaction. More specifically, the relative proportions of the ester and metal carboxylate or hydroxide which are admixed and reacted together are determined by stoichiometric considerations which are a function of the valence of the metal of the metal carboxylate, and the mole fraction of hemi- or diester components in the ester.

Thus, when using a divalent metal in the form of a metal carboxylate and a diester, the ester and metal carboxylate are mixed at about a 1:1 mole ratio.

Likewise, about a 2:1 molar ratio of ester:metal carboxylate would be employed using a divalent metal and hemiester.

In short, typically each equivalent of free acid on the ester is admixed with about $X^{-1}$ moles of metal carboxylate or hydroxide, where X is the valence of the metal in the metal carboxylate. The metal carboxylate or hydroxide and ester are allowed to react completely at a temperature of from about 25° to about 80° C. until the metal ester salt precipitates from the reaction mixture. The precipitate is typically then washed with a volatile solvent and dried under a nitrogen atmosphere.

The preferred method of salt formation is described in U.S. patent application Ser. No. 750,174, filed 7-1-85, the disclosure of which is herein incorporated by reference.

The metal salt of the ester has been found to possess anti-oxidant, anti-corrosion, and friction modification properties, and its primary utility is as a multifunctional additive in automatic transmission fluids.

As indicated above, a typical ATF composition contains the following components:

| Components | Vol % | Wt % |
| --- | --- | --- |
| V.I. Improver | 1–15 | 1–16 |
| Corrosion Inhibitor | 0.01–1 | 0.01–1.5 |
| Oxidation Inhibitor | 0.01–1 | 0.01–1.5 |
| Dispersant | 0.5–10 | 0.5–11 |
| Pour Point Depressant | 0.01–1 | 0.01–1.5 |
| Demulsifier | 0.001–0.1 | .001–0.15 |
| Anti-Foaming Agents | 0.001–0.1 | .001–0.15 |
| Anti-Wear Agents | 0.001–1 | .001–1.5 |
| Seal Swellant | 0.1–5 | 0.1–6 |
| Friction Modifiers | 0.01–1 | 0.1–1.5 |
| Mineral Oil Base | Balance | Balance |

Typical base oils for automatic transmission and other power transmitting fluids include a wide variety of light hydrocarbon mineral oils, such as, naphthenic base, paraffin base and mixtures thereof, having a lubricating viscosity range of about 34 to 150 (e.g., 75–150) SUS (Saybolt Universal Seconds) at 38° C.

Conventional additives of the above types for use in automatic transmission fluids are disclosed in U.S. Pat. No. 4,396,518.

As a result of the multifunctional properties possessed by the metal salt ester additives of the present invention, the use of separate corrosion inhibitors, oxidation inhibitors, and friction modifiers can be eliminated in lieu of employing the additive described herein. This simplifies the final ATF composition and reduces the possibility of adverse interaction between the components employed therein.

Furthermore, because of the more stringent requirements of ATF formulations relative to friction modification, the metal salt additives of the present invention can be employed in a variety of other compositions such as hydraulic fluids, heavy duty power transmitting fluids, power steering fluids, tractor universal oils, and the like wherein strict friction modification properties are not a requirement. Such fluids are referred to herein generically as power transmitting fluids.

In a broad sense therefore, the metal salt ester is employed in a power transmitting fluid comprising a major amount of a liquid hydrocarbon of lubricating viscosity, and a minor amount of said metal salt ester effective to impart one or more of the properties of corrosion inhibition, oxidation inhibition and friction modification relative to the absence of said additive. Additional conventional additives selected to meet the particular requirements of a selected type of power transmitting fluid can be included as desired.

More specifically, while the metal salt ester additive can be employed in the above-described fluid compositions in any effective amount, it is contemplated that such effective amount constitute typically from about 0.05 to about 2, preferably from about 0.1 to about 0.5, and most preferably from about 0.3 to about 0.4%, by weight, based on the total weight of the composition into which it is added.

When employed in an ATF formulation, such effective amounts can constitute from about 0.5 to about 2, preferably from about 0.1 to about 1, and most preferably from about 0.35 to about 0.6% (e.g., 0.5 to 0.6%), by weight, based on the weight of the ATF.

The following examples are given as specific illustrations of the claimed invention. It should be understood, however, that the invention is not limited to the specific details set forth in the examples. All parts and percentages in the examples as well as in the remainder of the specification are by weight unless otherwise specified.

EXAMPLE 1

The diester of a 2-octadecenyl succinic anhydride with 2,2'-thiobisethanol was prepared by adding 0.5 mole of the alcohol to a mole of the anhydride at 120° C. The reaction mixture was stirred at this temperature until the anhydride carbonyl adsorption band is absent in the IR spectrum of the reaction mixture. This compound can be represented by the formula:

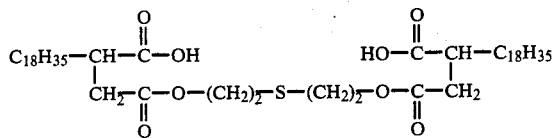

This ester was used to make the metal salt derivatives reported in Examples 2, 3, and 4.

EXAMPLE 2

1 mole of Mg (CH$_3$(C:O)O)$_2$4H$_2$O was dissolved in 1.5 liter CH$_3$OH at 35°–40° C. and 1 mole of the ester of Example 1 was dissolved in 2 liters CH$_3$OH at 60°–65° C. The magnesium acetate solution was gradually added to the solution of diester at about 60°–65° C. and stirred for an additional 5 to 10 minutes. When the desired magnesium salt product precipitated from solution, the methanol solution was decanted. The product was washed four times with methanol to remove acetic acid completely, and dried. The product was obtained in a yield of 92.9% and can be represented by the formula:

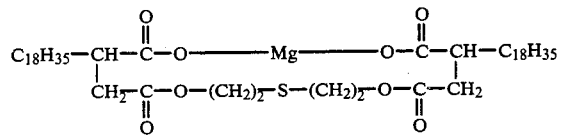

EXAMPLE 3

Following the procedure of Example 2, the analogous calcium salt monohydrate was prepared by reacting equimolar quantities of calcium acetate hydrate as a 50% aqueous methanol solution and the ester of Example 1 using methanol as the diluent. Yield of product was 87.8%.

EXAMPLE 4

Another calcium salt was prepared utilizing the same procedure employed in the foregoing examples, except that calcium propionate dissolved in 90% methanol was used as the reactant. The mole ratios were the same. Yield of product improved to 98.8%.

EXAMPLE 5

An automatic transmission fluid containing a conventional base oil as well as a conventional: dispersant, calcium-based detergent, seal sweller, oxidation inhibitor, corrosion inhibitor and viscosity improver, was formulated to act as a basis for comparison in evaluating the friction modification properties of the same according to General Motors Corporation Specification GM 6137-M, as modified according to current specifications. The particular procedure employed is a High-Energy Friction Characteristics and Durability test referred to herein as HEFCAD. This test uses a SAE No. 2 Friction Machine operated successfully for 100 hours wherein no unusual clutch plate wear or composition-face plate flaking occurs. After a break-in period of 24 hours, the test is conducted in a continuous series of 20 second cycles, each cycle consisting of three phases as follows: Phase I (10 seconds)—motor on at speed of 3,600 rpm, clutch plates disengaged; Phase II (5 seconds)—motor off, clutch plates engaged; and Phase III (5 seconds)—motor off, clutch released. The cycles are repeated for 75 hours after the break-in or until failure. To pass this test: between 14 and 100 hours of operation: (a) the level of kinetic torque, measured midway between the start and end of clutch engagement, should be at least 135 N·m; (b) the difference between the static torque and kinetic torque (as measured in (a) above) should not exceed 0 N·m; and (c) the engagement or lock-up time, i.e., time in Phase II it takes for motor speed to go from 3,600 to 0 to rpm with clutch engaged, should not exceed 0.65 seconds.

Accordingly, the ATF base formulation was tested in accordance with the HEFCAD procedure and the results summarized at Table 1, as Run 1.

To the base formulation of Run 1 was added 0.8 wt%, based on the weight of base formulation+ester, of the ester prepared in accordance with Example 1 and the resulting formulation tested by the HEFCAD procedure. The results are summarized at Table 1, Run 2.

Likewise, to separate samples of the base formulation of Run 1 was added the Mg or Ca salt ester additives of Examples 2 to 4 respectively in amounts as shown at Table 1, based on the weight of base formulation+metal salt additive. The resulting formulations were tested by the HEFCAD procedure and results summarized at Table 1, Runs 3 to 5.

EXAMPLE 6

Runs 2 to 4 were repeated with the exception that the wt% of the additive was reduced to 0.35% in the base formulation. The results of the HEFCAD test for these formulations are summarized at Table 1, Runs 6 to 8.

TABLE 1

| Run No. | Corresponding Ex. No. For Additive Prep. | Ester Additive Type | Wt % of Additive in Base Formulation | Lock-Up Time (sec) | Kinetic Torque (N · m) | Static Torque - Kinetic Torque (N · m) |
|---|---|---|---|---|---|---|
| 1 | 5 (Base Formulation) | None | 0 | .43 | 165 | +30 |
| 2 | 1 | Free Diester | 0.8 | .75 | 117 | 0 |
| 3 | 2 | Mg Diester Salt | 0.6 | .65 | 136 | −9 |
| 4 | 3 | Ca Diester Salt | 0.5 | .61 | 141 | −4 |
| 5 | 4 | Ca Diester Salt | 0.4 | .61 | 144 | +3 |
| 6 | 1 | Free Diester | 0.35 | .60 | 135 | +12 |
| 7 | 2 | Mg Diester Salt | 0.35 | .60 | 129 | +7 |
| 8 | 3 | Ca Diester Salt | 0.35 | .60 | 138 | +3 |

Referring to Table 1, it will be observed that the friction modification properties as defined by the HEFCAD test are concentration dependent. However, whereas the free diester of Run 1 fails both the lock-up and kinetic torque at a 0.8% concentration, the Mg and Ca ester salts of Runs 3 and 4 pass all three elements of the test even at lower concentrations of 0.6 and 0.5%. Thus, on a relative basis, the metal salt esters are more effective than the corresponding free esters. Moreover, it will be observed that the calcium salt performs better than the magnesium salt particularly at lower concentration levels of about 0.35%. While all the additives of Runs 6 to 8 all fail at least one element of the HEFCAD test at a concentration of 0.35%, the magnesium and calcium salts still outperform the free ester with respect to static-kinetic torque and such concentrations find utility in formulations where the friction modification properties are not as stringent.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An oil soluble composition of matter comprising at least one alkaline earth metal salt of an ester compound wherein the alkaline earth metal is calcium or magnesium, said ester compound being formed by the reaction of:

(A) an alcohol represented by the structural formula:

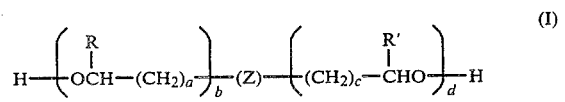
   (I)

wherein R and R' each independently can represent hydrogen, or a $C_1$ to about $C_6$ alkyl group; (a), (b), (c), and (d) each independently represent a number which can vary from 1 to about 3; and Z is a linking group selected from —O— and >$NR_1$ wherein $R_1$ can represent hydrogen, $C_1$ to about $C_4$ alkyl, or $C_1$ to about $C_4$ monohydroxy substituted alkyl; and (B) from about 1 to about 2 moles per mole of alcohol of an acid or anhydride represented by the respective structural formulas:

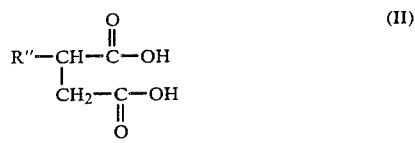
   (II)

and

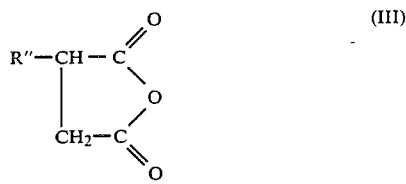
   (III)

wherein R" is an aliphatic hydrocarbon group containing from about 12 to about 50 carbons.

2. The composition of claim 1 wherein the R" group of formulas II and III is straight chain aliphatic.

3. The composition of claim 1 wherein in structural formula I (a), (b), (c), and (d), are 1, R and R' are independently hydrogen, methyl, or ethyl; and in structural formulas II and III, R" is a $C_{16}$ to $C_{30}$ straight chain aliphatic group.

4. The composition of claim 1 wherein Z in formula I is >$NR_1$ and $R_1$ is —$(CH_2)_2$—OH.

5. The composition of claim 1 wherein in structural formulas II and III R" contains from 18 to 22 carbon atoms, and R and R' in formula I independently represent hydrogen, methyl, or ethyl.

6. The composition of claim 1 wherein in structural formula I R and R' are hydrogen, and R" is a straight chain aliphatic group containing from about 16 to about 30 carbon atoms.

7. A composition of claim 1 wherein in structural formula I the numbers of (a) and (c) are the same, the numbers of (b) and (d) are the same, and R and R' are the same.

8. An oil soluble composition of matter comprising an alkaline earth metal salt of a monoester compound, a diester compound or mixtures of said compounds wherein the alkaline earth metal is calcium or magnesium, said compounds being formed by the reaction of:

(A) an alcohol represented by the structural formula:

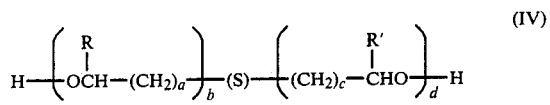

(IV)

wherein R and R' each independently can represent hydrogen, methyl, or ethyl; (a), (b), (c), and (d) each independently represent a number of from 1 to 3; and (B) an acid or anhydride represented by the respective structural formulas:

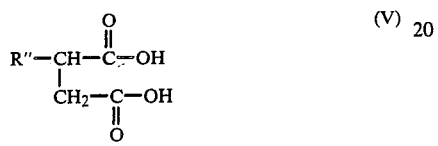

(V)

and

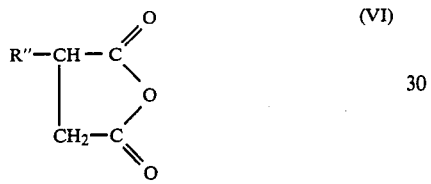

(VI)

wherein R″ is a $C_{12}$ to $C_{50}$ aliphatic hydrocarbon group.

9. The composition of claim 8 wherein the hydrocarbon group of R″ contains from about 18 to about 22 carbon atoms.

10. The composition of claim 8 wherein the ester is a diester.

11. The composition of claim 8 wherein the numbers representing (a), (b), (c), and (d) are 1.

12. The composition of claim 8 wherein the metal of the salt is calcium or magnesium, R″ contains from about 18 to about 22 carbon atoms, R and R' are hydrogen, and (a), (b), (c), and (d), are 1.

13. The composition of claim 12 wherein R″ contains 18 carbon atoms.

14. The composition of claim 8 wherein R and R' are the same, the numbers represented by (a) and (c) are the same, the numbers represented by (b) and (d) are the same.

15. The composition of claim 8 wherein the metal of the salt is calcium, the alcohol of structural formula IV is thio-bis-ethanol, and R″ of structural formulas V or VI is octadecenyl.

16. A power transmitting fluid comprising a major amount of liquid hydrocarbon mineral oil of lubricating viscosity and at least one metal salt ester additive, said additive comprising an alkaline earth metal salt of at least one ester compound, said ester compound being formed by the reaction of:

(A) an alcohol represented by the structural formula:

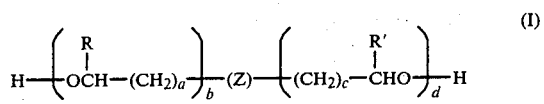

(I)

wherein R and R' each independently can represent hydrogen or a $C_1$ to about $C_6$ alkyl group; (a), (b), (c), and (d) each independently represent a number which can vary from 1 to about 3; and Z represents a linking group selected from —O— and >NR$_1$, wherein R$_1$ can represent hydrogen, about $C_1$ to $C_4$ alkyl, or $C_1$ to about $C_4$ monohydroxy substituted alkyl; and (B) from about 1 to about 2 moles per mole of alcohol of an acid or anhydride represented by the respective structural formulas:

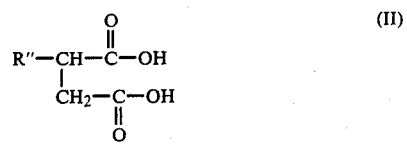

(II)

and

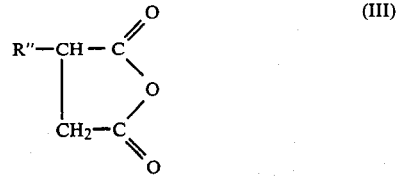

(III)

wherein R″ is an aliphatic hydrocarbon group containing from about 12 to about 50 carbons; said alkaline earth metal salt being present in an amount effective to impart to said fluid one or more of rust inhibition, oxidation inhibition and friction modification relative to the absence of said salt.

17. The power transmitting fluid of claim 16 wherein said fluid is adapted for use as an automatic transmission fluid containing a friction modifying amount of said additive and the metal of said metal salt is selected from the group consisting of calcium, magnesium, and mixtures thereof.

18. The automatic transmission fluid of claim 17 wherein said friction modifying amount is from about 0.35 to about 0.6%, by weight, based on the weight of said fluid.

19. A power transmitting fluid comprising a major amount of liquid hydrocarbon mineral oil of lubricating viscosity and at least one metal salt ester additive, said additive comprising an alkaline earth metal salt of a monoester compound, a diester compound or mixtures of said compounds, said compounds being formed by the reaction of:

(A) an alcohol represented by the structural formula:

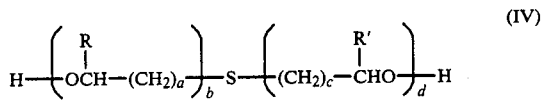

(IV)

wherein R and R' each independently can represent hydrogen methyl, or ethyl; (a), (b), (c), and (d)

each independently represent a number from 1 to 3; and (B) an acid or anhydride represented by the respective structural formulas:

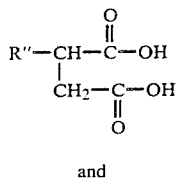 (V)

and

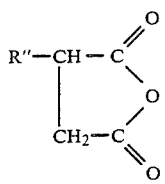 (VI)

wherein R" is a $C_{12}$ to $C_{50}$ aliphatic hydrocarbon group said alkaline earth metal salt being present in an amount effective to impart to said fluid one or more of rust inhibition, oxidation inhibition and friction modification relative to the absence of said salt.

20. The fluid of claim 19 wherein in said additive the hydrocarbon group of R" contains from about 18 to about 22 carbon atoms.

21. The fluid of claim 19 wherein in said additive the metal of said salt is selected from the group consisting of calcium and magnesium.

22. The fluid of claim 19 wherein in said additive the ester is a diester.

23. The fluid of claim 19 wherein in said additive the numbers representing (a), (b), (c), and (d), are 1.

24. The fluid of claim 19 wherein in said additive the metal of the salt is calcium, magnesium, or mixtures thereof, R" contains from about 18 to about 22 carbon atoms, R and R' are hydrogen, and (a), (b), (c), and (d), are 1.

25. The fluid of claim 24 wherein in said additive R" contains 18 carbon atoms.

26. The fluid of claim 19 wherein in said additive R and R' are the same, the numbers represented by (a) and (c) are the same, and the numbers represented by (b) and (d) are the same.

27. The fluid of claim 19 wherein in said additive the metal of the salt is calcium, the alcohol of structural formula IV is thio-bis-ethanol, and R" of structural formulas V or VI is octadecenyl.

28. The fluid of claim 19 wherein said fluid is adapted for use as an automatic transmission fluid and said additive is present in a friction modifying amount.

29. The automatic transmission fluid of claim 28 wherein said friction modifying amount is from about 0.35 to about 0.6%, by weight, based on the weight of the fluid.

30. A power transmitting fluid comprising a major amount of a liquid hydrocarbon mineral oil of lubricating viscosity and at least one metal salt ester additive, said additive comprising an alkaline earth metal salt of at least one ester compound wherein the alkaline earth metal salt is a salt of calcium, magnesium or mixture thereof, said ester compound being formed by the reaction of:

(A) an alcohol represented by the structural formula:

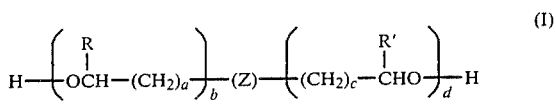 (I)

wherein R and R' each independently can represent hydrogen or a $C_1$ to about $C_6$ alkyl group; (a), (b), (c), and (d) each independently represent a number which can vary from 1 to about 3; and Z represents a linking group selected from —O— and $>NR_1$, wherein $R_1$ can represent hydrogen, about $C_1$ to $C_4$ alkyl, or $C_1$ to about $C_3$ monohydroxy substituted alkyl; and (B) from about 1 to about 2 moles per mole of alcohol of an acid or anhydride represented by the respective structural formulas:

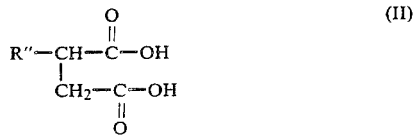 (II)

and

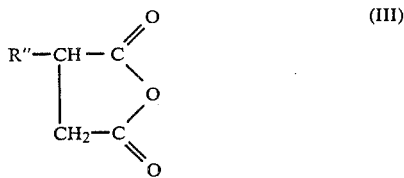 (III)

wherein R" is an aliphatic hydrocarbon group containing from about 12 to about 50 carbons said alkaline earth metal salt being present in an amount effective to impart to said fluid one or more of rust inhibition, oxidation inhibition and friction modification relative to the absence of said salt.

31. The automatic transmission fluid of claim 30 wherein said friction modifying amount is from about 0.35 to about 0.6%, by weight, based on the weight of said fluid.

32. A power transmitting fluid comprising a major amount of a liquid hydrocarbon mineral oil of lubricating viscosity and at least one metal salt ester additive, said additive comprising an alkaline earth metal salt of a monoester compound, a diester compound or mixtures of said compounds wherein the alkaline earth metal salt is a salt of calcium, magnesium or mixtures thereof, said compounds being formed by the reaction of:

(A) an alcohol represented by the structural formula:

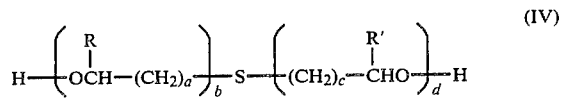 (IV)

wherein R and R' each independently can represent hydrogen, methyl, or ethyl; (a), (b), (c), and (d) each independently represent a number of from 1 to 3; and (B) an acid or anhydride represented by the respective structural formulas:

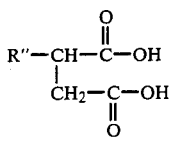

(V)

and

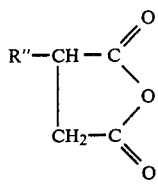

(VI)

wherein R″ is a $C_{12}$ to $C_{50}$ aliphatic hydrocarbon group said additive being present in an amount effective to impart to said fluid one or more of rust inhibition, oxidation inhibition and friction modification relative to the absence of said salt.

33. The fluid of claim 32 wherein in said additive the hydrocarbon group of R″ contains from about 18 to 22 carbon atoms.

34. The fluid of claim 32 wherein in said additive the ester is a diester.

35. The fluid of claim 32 wherein in said additive the numbers representing (a), (b), (c), and (d), are 1.

36. The fluid of claim 32 wherein in said additive the metal of the salt is calcium, magnesium, or mixtures thereof, R″ contains from about 18 to about 22 carbon atoms, R and R′ are hydrogen, and (a), (b), (c), and (d), are 1.

37. The fluid of claim 36 wherein said additive R″ contains 18 carbon atoms.

38. The fluid of claim 32 wherein in said additive R and R′ are the same, the numbers represented by (a) and (c) are the same, and the numbers represented by (b) and (d) are the same.

39. The fluid of claim 32 wherein in said additive the metal of the salt is calcium, the alcohol of structural formula IV is thio-bis-ethanol, and R″ of structural formulas V or VI is octadecenyl.

40. The automatic transmission fluid of claim 32 wherein said friction modifying amount is from about 0.35 to about 0.6%, by weight, based on the weight of the fluid.

41. A process for modifying at least one of the oxidative stability and friction characteristics of a power transmitting fluid comprising a major amount of liquid hydrocarbon mineral oil of lubricating viscosity which comprises adding at least one metal salt ester additive to said fluid, said additive comprising an alkaline earth metal salt of at least one ester compound wherein said alkaline earth metal is calcium, magnesium or mixtures thereof, said ester compound being formed by the reaction of:

(A) an alcohol represented by the structural formula:

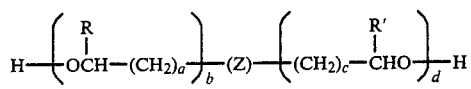

(I)

wherein R and R′ each independently can represent hydrogen or a $C_1$ to about $C_6$ alkyl group; (a), (b), (c), and (d) each independently represents a number which can vary from 1 to about 3; and Z represents a linking group selected from —O— and $NR_1$, wherein $R_1$ can represent hydrogen, about $C_1$ to $C_4$ alkyl, or $C_1$ to about $C_4$ monohydroxy substituted alkyl; and (B) from about 1 to about 2 moles per mole of alcohol of an acid or anhydride represented by the respective structural formulas:

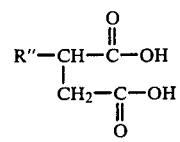

(II)

and

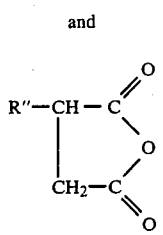

(III)

wherein R″ is an aliphatic hydrocarbon group containing from about 12 to about 50 carbons said additive being present in an amount effective to impart to said fluid at least one of rust inhibition, oxidative inhibition and friction modification relative to the absence of said additive.

42. The process according to claim 41 wherein said fluid is adapted for use as an automatic transmission fluid containing a friction modifying amount of said additive and the metal of said metal salt is selected from the group consisting of calcium, magnesium, and mixtures thereof.

43. The process according to claim 42 wherein said friction modifying amount is from about 0.35 to about 0.6%, by weight, based on the weight of said fluid.

44. A process for improving at least one of oxidative stability and friction characteristics of a power transmitting fluid comprising a major amount of a liquid hydrocarbon mineral oil of lubricating viscosity which comprises adding at least one metal salt ester additive to said fluid, said additive comprising an alkaline earth metal salt of a monoester compound, wherein said alkaline earth metal is calcium, magnesium or mixtures thereof, a diester compound or mixtures of said compounds, said compounds being formed by the reaction of:

(A) an alcohol represented by the structural formula:

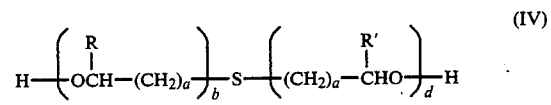

(IV)

wherein R and R′ each independently can represent hydrogen, methyl, or ethyl; (a), (b), (c), and (d) each independently represent a number of from 1 to 3; and (B) an acid or anhydride represented by the respective structural formulas:

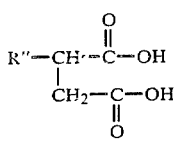
(V)

and

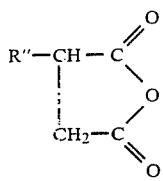
(VI)

wherein R" is a $C_{12}$ to $C_{50}$ aliphatic hydrocarbon group; said additive being present in an amount effective to impart to said fluid at least one of rust inhibition, oxidative inhibition and friction modification relative to the absence of said additive.

45. The process according to claim 44 wherein in said additive the hydrocarbon group of R" contains from about 18 to about 22 carbon atoms.

46. The process according to claim 44 wherein in said additive the metal of the salt is selected from the group consisting of calcium and magnesium.

47. The process according to claim 44 wherein in said additive the ester is a diester.

48. The process according to claim 44 wherein in said additive the numbers representing (a), (b), (c), and (d), are 1.

49. The process according to claim 44 wherein in said additive the metal of the salt is calcium, magnesium, or mixtures thereof, R" contains from about 18 to about 22 carbon atoms, R and R' are hydrogen, and (a), (b), (c), and (d), are 1.

50. The process according to claim 49 wherein in said additive R' contains 18 carbon atoms.

51. The process according to claim 44 wherein in said additive R and R' are the same, the numbers represented by (a) and (c) are the same, and the numbers represented by (b) and (d) are the same.

52. The process according to claim 44 wherein in said additive the metal of the salt is calcium, the alcohol of structural formula IV is thio-bis-ethanol, and R" of structural formulas V or VI is octadecenyl.

53. The process according to claim 44 wherein said fluid is adapted for use as an automatic transmission fluid and said additive is present in a friction modifying amount.

54. The process according to claim 53 wherein said friction modifying amount is from about 0.35 to about 0.6%, by weight, based on the weight of the fluid.

* * * * *